US009012162B2

(12) United States Patent
Gangadharan et al.

(10) Patent No.: US 9,012,162 B2
(45) Date of Patent: Apr. 21, 2015

(54) CLINICAL DIAGNOSIS OF HEPATIC FIBROSIS USING A NOVEL PANEL OF HUMAN SERUM PROTEIN BIOMARKERS

(75) Inventors: Bevin Gangadharan, Oxford (GB); Nicole Zitzmann, Oxford (GB); Raymond A. Dwek, Oxford (GB)

(73) Assignee: The Chancellor, Masters and Scholars of The University of Oxford, Oxford (GB)

(*) Notice: Subject to any disclaimer, the term of this patent is extended or adjusted under 35 U.S.C. 154(b) by 0 days.

(21) Appl. No.: 11/851,619

(22) Filed: Sep. 7, 2007

(65) Prior Publication Data

US 2008/0085526 A1   Apr. 10, 2008

Related U.S. Application Data

(60) Provisional application No. 60/842,980, filed on Sep. 8, 2006.

(51) Int. Cl.
*G01N 33/00* (2006.01)
*G01N 33/576* (2006.01)

(52) U.S. Cl.
CPC .......... *G01N 33/576* (2013.01); *G01N 33/5767* (2013.01); *G01N 2800/085* (2013.01); *Y10S 436/811* (2013.01)

(58) Field of Classification Search
None
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,275,149 A | 6/1981 | Litman et al. | |
| 4,277,437 A | 7/1981 | Maggio | |
| 4,366,241 A | 12/1982 | Tom et al. | |
| 4,959,314 A | 9/1990 | Mark et al. | |
| 5,571,894 A | 11/1996 | Wels et al. | |
| 5,583,055 A * | 12/1996 | Oh et al. | 436/517 |
| 5,587,458 A | 12/1996 | King et al. | |
| 6,631,330 B1 * | 10/2003 | Poynard | 702/19 |
| 6,986,995 B2 * | 1/2006 | Rose et al. | 435/7.1 |
| 7,244,619 B2 | 7/2007 | Contreras et al. | |
| 7,365,170 B2 * | 4/2008 | Cooper et al. | 530/399 |
| 7,972,802 B2 * | 7/2011 | Heinecke et al. | 435/7.21 |
| 8,093,017 B2 | 1/2012 | Pugia | |
| 2003/0199000 A1 * | 10/2003 | Valkirs et al. | 435/7.1 |
| 2003/0216544 A1 * | 11/2003 | Harley | 530/324 |
| 2005/0136489 A1 | 6/2005 | Tseng et al. | |
| 2006/0084059 A1 | 4/2006 | Yip et al. | |
| 2006/0115476 A1 * | 6/2006 | Tedesco et al. | 424/144.1 |
| 2006/0178306 A1 * | 8/2006 | Bowser | 514/12 |
| 2007/0099242 A1 * | 5/2007 | Heinecke et al. | 435/7.2 |
| 2007/0117100 A1 | 5/2007 | Tsai | |
| 2007/0142413 A1 | 6/2007 | Block et al. | |
| 2007/0178442 A1 * | 8/2007 | Wienhues-Thelen et al. | 435/4 |
| 2007/0218519 A1 | 9/2007 | Urdea et al. | |
| 2008/0161203 A1 | 7/2008 | Su et al. | |
| 2009/0035801 A1 | 2/2009 | Goldknopf et al. | |

FOREIGN PATENT DOCUMENTS

| | | |
|---|---|---|
| CN | 1759320 A | 4/2006 |
| CN | 101003831 A | 7/2007 |
| CN | 101326439 A | 12/2008 |
| TW | 200521139 A | 7/2005 |
| WO | WO 93/16185 A2 | 8/1993 |
| WO | WO 02/16949 A1 | 2/2002 |
| WO | WO 03/073822 A2 | 9/2003 |
| WO | WO 2005/055925 A2 | 6/2005 |
| WO | WO 2005/116901 A2 | 12/2005 |
| WO | WO 2006/082522 A1 | 8/2006 |
| WO | WO 2006/089586 A1 | 8/2006 |
| WO | WO 2006/121892 A2 | 11/2006 |
| WO | WO 2010/079253 A2 | 7/2010 |
| WO | WO 2010/081729 A1 | 7/2010 |

OTHER PUBLICATIONS

Adams et al., Hepascore: An Accurate Validated Predictor of Liver Fibrosis in Chronic Hepatitis C Infection, Clinical Chemistry 51:10 Oct. 2005, pp. 1867-1873.*
Kawamoto et al., Assessment o liver fibrosis by a noninvasive method of transient elastography and biochemical markers, World Journal of Gastroenterology, 2006, Jul. 12(27), pp. 4325-4330.*
Gonias et al., Catabolic Pathways for Streptokinase, Plasmin, and Streptokinase Activator Complex in Mice, J. Clin. Invest, vol. 70, Aug. 1982, pp. 412-423.*
Rockey et al., Noninvasive Measures of Liver Fibrosis, Hepatology, vol. 43, No. 2, Suppl 1, Februrary 2006, pp. S113-S120.*
Tang et al., Regulation of complement C3 and C4 synthesis in human peritoneal mesothelial cells by peritoneal dialysis fluid, Clin Exp Immunol 2004; 136, pp. 85-94.*
Loeffler et al., Measurement by Elisa of Complement Factor 4 (C4) in the Rat Brain: Necessity for Removal of Cerebrovascular Proteins, Neurochem Res, Jul. 18, 2006, 31: pp. 999-1002.*

(Continued)

*Primary Examiner* — Gary W Counts
(74) *Attorney, Agent, or Firm* — Foley & Lardner LLP (57) ABSTRACT

The inventors have proposed a novel panel of human serum protein biomarkers for diagnosing hepatic fibrosis and cirrhosis. Presently there is no reliable non-invasive way of assessing liver fibrosis. A 2D-PAGE based proteomics study was used to identify potential fibrosis biomarkers. Serum from patients with varying degrees of hepatic scarring induced by infection with the hepatitis C virus (HCV) was analyzed. Several proteins associated with liver scarring and/or viral infection were identified. These proteins include the inter-α-trypsin inhibitor heavy chain H4 fragments, complement factor H-related protein 1, CD5L, Apo L1, and β2GPI. Increased and decreased thiolester cleavage of a2M and Complement C3, respectively, was also detected. The concentrations of these novel biomarkers can be determined using an immunoassay where the concentrations would reflect the extent of fibrosis. A fibrosis scoring scale for each of the novel biomarkers is proposed. The additive result from the scores of all the novel biomarkers would give a more reliable indication of the degree of fibrosis rather than examining individual biomarkers.

22 Claims, 2 Drawing Sheets

(56) References Cited

OTHER PUBLICATIONS

Kamada et al., Enhanced Carbon Tetrachloride-induced Liver Fibrosis in Mice Lacking adiponectin, Gastroenterolgoy, 2003; 125, pp. 1796-1807.*
Cai et al., "Identification of mouse *itih-4* encoding a glycoprotein with two EF-hand motifs from early embryonic liver," Biochimica et Biophysica Acta, 1998, 1398:32-37.
Fontana et al., "Noninvasive Monitoring of Patients With Chronic Hepatitis C," Hepatology, Nov. 2002, 36(5, Suppl. 1):S57-S64.
Imbert-Bismut et al., "Biochemical markers of liver fibrosis in patients with hepatitis C virus infection: a prospective study," The Lancet, Apr. 7, 2001, 357(9262):1069-1075.
Song et al., "Quantification of Fragments of Human Serum Inter-α-Trypsin Inhibitor Heavy Chain 4 by a Surface-Enhanced Laser Desorption/Ionization Based Immunoassay," Clinical Chemistry, Jun. 2006, 52(6):1045-1053.
Zhang et al., "Three Biomarkers Identified from Serum Proteomic Analysis for the Detection of Early Stage Ovarian Cancer," Cancer Research, Aug. 15, 2004, 64(16):5882-5890.
Drake et al., "Lectin Capture Strategies Combined with Mass Spectrometry for the Discovery of Serum Glycoprotein Biomarkers," Molecular & Cellular Proteomics, 2006, 1957-1967.
Gangadharan et al., "Novel Serum Biomarker Candidates for Liver Fibrosis in Hepatitis C Patients," 2007, Clinical Chemistry, 53(10):1792-1799.
Ishak et al., "Histological grading and staging of chronic hepatitis," 1995, Journal of Hepatology, 22: 696-699.
Nagaoka et al., "Hepatic clearance of tissue-type plasminogen activator and plasma kallikrein in experimental liver fibrosis," 2003, Liver International, 23: 476-483.
Pluckthun, A., "Antibodies from *Escherichia coli*," The Pharmacology of Monoclonal Antibodies 269-315 (Rosenburg and Moore eds. 1994).
Rimola et al., "Beneficial effect of drugs interfering with the renin-angiotensin system on the development of fibrosis in hepatitis C recurrence after liver transplantation (LT)," Am J Transplan, 2003, 5, 433, Abstract #1099.
Scatchard, George, "The attractions of proteins for small molecules and ions," Ann. NY Acad. Sci. 51: 660-672, 1949.
Steel et al., A strategy for the comparative analysis of serum proteomes for the discovery of biomarkers for hepatocellular carcinoma, 2003, Proteomics, 3:601-609.
Who, "Global surveillance and control of heptatitis C," J. Viral. Hepatitis, 1999; 6: 35-47.
U.S. Appl. No. 12/779,349, filed May 13, 2010, Gangadharan et al.
Invitation to Pay Additional Fees, partial International Search Report in PCT/IB2010/001343, Sep. 23, 2010, 8 pages.
International Search Report and Written Opinion in PCT/IB2010/001343, Nov. 2, 2010, 21 pags.
Albert et al., "Apolipoprotein L-I is positively associated with hyperglycemia and plasma triglycerides in CAD patients with low HDL," Journal of Lipid Research, 2005 (published JLR Papers in Press Dec. 16, 2004), 46(3):469-474.
Calès et al., "A Novel Panel of Blood Markers to Assess the Degree of Liver Fibrosis," Hepatology Dec. 2005, 42(6):1373-1381.
Fabris et al., "Low fibrosis progression of recurrent hepatitis C in apolipoprotein E ε4 carriers: relationship with the blood lipid profile," Liver International, 2005, 25(6):1128-1135.
Greer et al,. "Gene expression analysis in a canine model of X-linked Alport syndrome," Mammalian Genome, Sep. 8, 2006, 17(9):976-990.
Sadlier et al,. "Sequential Extracellular Matrix-focused and Baited-global Cluster Analysis of Serial Transcriptomic Profiles Identifies Candidate Modulators of Renal Tubulointerstitial Fibrosis in Murine Adriamycin-induced Nephropathy," J. Biol. Chem., Jul. 9, 2004 (published JBC Papers in Press Mar. 18, 2004), 279(28):29670-29680.
Stakišaitis et al., "Blood serum apolipoproteins B and A-I in females suffering from rheumatic heart valve disease," Medicina, 2004, 40(1):33-37.
Vanhollebeke et al., "The function of apolipoproteins L," Cell. Mol. Life Sci., Jul. 17, 2006 [online], 63(17):1937-1944.
Gangadharan et al., "Discovery of Novel Biomarker Candidates for Liver Fibrosis in Hepatitis C Patients: A Preliminary Study," PLoS ONE, Jun. 2012, 7(6):e39603, 1-14.
Seth et al., "Gene Expression Profiling of Alcoholic Liver Disease in the Baboon (*Papio hahadryas*) and Human Liver," American Journal of Pathology, Dec. 2003, 163(6):2303-2317.
Qing et al., "Syndrome Indentification of CC4 Induced Liver Fibrosis Model Rats Based on Syndrome Detecting from Recipe Used," Chinese Journal of Integrated Traditional and Western Medicine, Mar. 31, 2009, 29:246-250, with English abstract on first page, English portions only.

* cited by examiner

CLINICAL DIAGNOSIS OF HEPATIC FIBROSIS USING A NOVEL PANEL OF HUMAN SERUM PROTEIN BIOMARKERS

CROSS-REFERENCE TO RELATED APPLICATIONS

This application claims priority to U.S. Provisional Application No. 60/842,980 filed Sep. 8, 2006, the disclosure of which is incorporated herein by reference in its entirety.

FIELD OF INVENTION

The present application relates generally to methods for diagnosing hepatic fibrosis using a panel of antibodies targeted against a novel panel of fibrosis biomarkers. These novel proteins may also serve as biomarkers for hepatitis and hepatocellular carcinoma (HCC) as well as drug targets for hepatic scarring and HCC.

BACKGROUND OF THE INVENTION

Hepatic fibrosis. Hepatic fibrosis (liver fibrosis) is a wound healing response characterised by the excessive accumulation of scar tissue (i.e. extracellular matrix) in the liver. Normal structural elements of tissues are replaced with excessive amounts of non-functional scar tissue. Needle liver biopsy is the primary tool for the diagnosis and assessment of fibrosis yet there are a number of well-documented limitations and disadvantages to this technique including patient discomfort, pain, bleeding, and death in rare cases. Furthermore, a biopsy can be unreliable if fibrosis is not homogenous throughout the liver. Hepatic fibrosis can be caused by various factors including alcohol and viruses.

Cirrhosis. Hepatic cirrhosis is the most severe form of liver scarring and, unlike hepatic fibrosis, is generally considered to be irreversible and nodular. Cirrhosis is the cause of over 6000 deaths every year in the UK and approximately 27,000 in the USA, making it the ninth leading cause of death (MacSween et al., (2002), Pathology of the Liver, 4th Edition, Churchill Livingstone). Cirrhosis is a major risk factor for HCC and, at this stage of liver cancer, the only curative approach is liver transplantation. In the case of virally induced liver cancer, hepatic scarring and HCC can recur after transplantation. It is imperative to diagnose fibrosis in the early stages of reversible liver scarring so that irreversible cirrhosis can be prevented.

Hepatitis C virus. Approximately 170 million people worldwide, i.e. 3% of the world's population (see e.g. WHO, J. Viral. Hepat. 1999; 6: 35-47), and approximately 4 million people in the United States are infected with Hepatitis C virus (HCV, HepC). HCV is of the leading causes of hepatic fibrosis and cirrhosis. About 80% of individuals acutely infected with HCV become chronically infected. Hence, HCV is a major cause of chronic hepatitis. Once chronically infected, the virus is almost never cleared without treatment. In rare cases, HCV infection causes clinically acute disease and even liver failure. Chronic HCV infection can vary dramatically between individuals, where some will have clinically insignificant or minimal liver disease and never develop complications and others will have clinically apparent chronic hepatitis and may go on to develop fibrosis and cirrhosis. About 20% of individuals with HCV who do develop cirrhosis will develop end-stage liver disease and have an increased risk of developing primary liver cancer.

There is a need for improved methods of diagnosing hepatic fibrosis and cirrhosis in patients

SUMMARY OF THE INVENTION

The present invention provides methods for the detection of fibrosis.

In one embodiment, the invention provides a method of detecting fibrosis, comprising: (a) determining the level of a HF-ASSOCIATED polypeptide in a biological sample obtained from a patient; and (b) comparing said level (a) to a control level of said HF-ASSOCIATED polypeptide in order to determine a positive or negative diagnosis of said fibrosis. These biomarkers may be applied to any disease which displays fibrosis such as hepatic fibrosis, renal fibrosis, cardial fibrosis, skin fibrosis, pancreatic fibrosis etc. but in specific embodiments the fibrosis is hepatic fibrosis. Preferably, the polypeptide is selected from the group consisting of: inter-α-trypsin inhibitor heavy chain H4 fragments, α1 antichymotrypsin, apolipoprotein L1 (Apo L1), prealbumin, albumin, isoforms of CD5 antigen like protein (CD5L), β2 glycoprotein I (β2GPI), α2 macroglobulin (a2M) and immunoglobulin components, α1, α2 and β chains of haptoglobin, complement components (C3, C4 and factor H-related protein 1), adiponectin, ApoE, prothrombin, clusterin, and angiotensinogen. In other embodiments, the fibrosis includes differential regulation of HF-ASSOCIATED polypeptides. In other embodiments, the sample is taken from blood serum or plasma.

In another embodiment, the current invention provides a method for detecting a HF-ASSOCIATED polypeptide comprising: a) isolating a biological sample from a patient with fibrosis, b) isolating a biological sample from a patient without fibrosis, c) analyzing the samples from a) and b) using 2D-PAGE, and d) comparing the 2D-PAGE results to identify polypeptides with differential expression between patients with and without fibrosis.

In another embodiment, the current invention provides a method for scaling the severity of fibrosis comprising: a) determining the level of at least one HF-ASSOCIATED polypeptide in a biological sample obtained from a patient; and b) comparing said level of HF-ASSOCIATED polypeptides in said patient biological sample to the predetermined level of said HF-ASSOCIATED polypeptides in a population of patients ranging from no fibrosis to cirrhosis.

In another embodiment, the current invention provides a kit useful for the prognosis of fibrosis, comprising a HF-ASSOCIATED agent wherein the agent specifically detects HF-ASSOCIATED polypeptides. In specific embodiments, the agent is an antibody or functional equivalent thereof that binds HF-ASSOCIATED polypeptides. These antibodies may be used to perform an ELISA assay. The kit may further comprise at least one target specifically for detecting another gene or gene product useful as a prognostic indicator.

In another embodiment, the current invention provides a method of determining the prognosis of fibrosis, comprising: (a) determining the level of a HF-ASSOCIATED polypeptide in a biological sample obtained from a patient; and (b) comparing said level of (a) to a control level of said HF-ASSOCIATED polypeptide in order to determine a positive or negative diagnosis of said fibrosis.

BRIEF DESCRIPTION OF THE DRAWINGS

FIGS. 1 to 4 These figures show the changes observed in expression of the main novel biomarkers. Each image shows a magnified region of the 2D-PAGE gel with the relative position of the identified protein circled. Representative serum gel images are shown for healthy individuals and patients with cirrhosis.

FIG. 1 CD5 antigen-like protein is shown to be absent in normal serum but present in serum from cirrhotic patients, FIG. 2 Apolipoprotein L1 is shown to be present in normal serum but absent in serum from cirrhotic patients, FIG. 3 Inter-α-trypsin inhibitor heavy chain H4. This inhibitor was found to be cleaved into 35 and 70 kDa fragments in serum samples from normal individuals. Serum from cirrhosis patients showed absence of the 35 kDa fragment and decreased expression of the 70 kDa fragment suggesting decreased cleavage of this protein.

DETAILED DESCRIPTION OF THE PREFERRED EMBODIMENTS

The following description outlines the invention summarized above. The invention, however, is not limited to the particular methodology, protocols, cell lines, animal species or genera, constructs, and reagents described and as such may vary. Likewise, the terminology used herein describes particular embodiments only, and is not intended to limit the scope of the invention.

The inventors have discovered that, various proteins are differentially expressed in human serum samples of HCV-induced fibrosis/cirrhosis patients when compared with healthy individuals. This discovery was achieved by comparing these serum samples using a technique that separates proteins in two dimensions on a gel matrix to give discrete protein spots.

Unless defined otherwise, all technical and scientific terms used herein have the same meaning as commonly understood to one of ordinary skill in the relevant art.

All publications and patents mentioned herein are hereby incorporated herein by reference for the purpose of describing and disclosing, for example, the constructs and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

a. DEFINITIONS

For convenience, the meaning of certain terms and phrases employed in the specification, examples, and appended claims are provided below.

The singular forms "a," "an," and "the" include plural reference unless the context clearly dictates otherwise.

"β2GPI" refers to $\beta_2$ glycoprotein I.

"2D-PAGE" refers to two dimensional polyacrylamide gel electrophoresis.

"a2M" refers to α2 macroglobulin.

"ABTS" refers to 2,2'-azino-bis(3-ethylbenzthiazoline-6-sulphonic acid).

"Apo L1" refers to apolipoprotein L1.

"BSA" refers to bovine serum albumin.

"CD5L" refers to CD5 antigen like protein.

"ELISA" refers to Enzyme Linked Immunosorbent Assay.

"HCC" refers to hepatocellular carcinoma.

"HCV" refers to hepatitis C virus.

"HF" refers to hepatic fibrosis

"HRP" refers to horseradish peroxidase.

"kDa" refers to kilodalton.

"LFT" refers to liver function test.

"PBS" refers to phosphate buffered saline.

"PBS-T" refers to Tween containing PBS solution.

"tPA" refers to tissue-type plasminogen activator.

"Biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived there from and the progeny thereof. Additionally, the term may encompass circulating tumor or other cells. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement, such as treatment with reagents, solubilization, or enrichment for certain components.

"Biomolecular sequence" or "sequence" refers to all or a portion of a polynucleotide or polypeptide sequence.

"BLAST" refers to Basic Local Alignment Search Tool, a technique for detecting ungapped sub-sequences that match a given query sequence. "BLASTP" is a BLAST program that compares an amino acid query sequence against a protein sequence database. "BLASTX" is a BLAST program that compares the six-frame conceptual translation products of a nucleotide query sequence (both strands) against a protein sequence database.

"Cancer," "neoplasm," and "tumor," used interchangeably herein, refer to cells or tissues that exhibit an aberrant growth phenotype characterized by a significant loss of control of cell proliferation. The methods and compositions of this invention particularly apply to precancerous (i.e., benign), malignant, pre-metastatic, metastatic, and non-metastatic cells.

A "fibrosis is characterized by the differential regulation of HF-ASSOCIATED polypeptides" refers to a subject with tissue that exhibits scarring, and in which a HF-ASSOCIATED protein has differential expression.

"Fibrosis phenotype" refers to any of a variety of biological phenomena that are characteristic of a fibrotic cell. The phenomena can vary with the type of fibrosis, but the fibrosis phenotype is generally identified by abnormalities in scar tissue formation.

"Cell type" refers to a cell from a given source (e.g., tissue or organ) or a cell in a given state of differentiation, or a cell associated with a given pathology or genetic makeup.

"Complementary" refers to the topological compatibility or matching together of the interacting surfaces of a probe molecule and its target. The target and its probe can be described as complementary, and furthermore, the contact surface characteristics are complementary to each other.

The term "detectable" refers to a polypeptide expression patterns which may observed using techniques described in this application and well known to a person of skill in the art.

For example, polypeptide expression may be "detected" via standard techniques including immunoassays such as Western blots.

"Diagnosis" and "diagnosing" generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states or fibrosis), and therametrics (e.g., monitoring a subject's condition to provide information as to the effect or efficacy of therapy).

"Differential expression" refers to both quantitative as well as qualitative differences in the temporal and tissue expression patterns of a gene. For example, a differentially expressed gene may have its expression activated or completely inactivated in normal versus disease conditions. Such a qualitatively regulated gene may exhibit an expression pattern within a given tissue, cell type, or in the serum/plasma of the subject that is detectable in either control or disease conditions, or detectable in both but with different expression. "Differentially expressed protein," as used herein, refers to an amino acid sequence that uniquely identifies a differentially expressed protein so that detection of the differentially expressed protein in a sample is correlated with the presence of a differentially expressed protein in a sample.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein or fragments thereof. The fragments may be produced via enzymatic cleavage or biological processes characteristic of normal or diseased conditions.

An "expression product" or "gene product" is a biomolecule, such as a protein or mRNA, that is produced when a gene in an organism is transcribed or translated or post-translationally modified.

A "fragment of a protein" refers to a portion of a protein. For example, fragments of proteins may comprise polypeptides obtained by digesting full-length protein isolated from cultured cells. In one embodiment, a protein fragment comprises at least about 6 amino acids. In another embodiment, the fragment comprises at least about 10 amino acids. In yet another embodiment, the protein fragment comprises at least about 16 amino acids.

In the context of this application, the term "functional equivalent" refers to a protein that possesses functional or structural characteristics that are substantially similar to all or part of the native HF-ASSOCIATED protein. The term "functional equivalent" is intended to include the "fragments," "mutants," "derivatives," "alleles," "hybrids," "variants," "analogs," or "chemical derivatives" of native HF-ASSOCIATED proteins.

In the context of immunoglobulins, the term "functional equivalent" refers to immunoglobulin molecules that exhibit immunological binding properties that are substantially similar to the parent immunoglobulin. "Immunological binding properties" refers to non-covalent interactions of the type that occurs between an immunoglobulin molecule and an antigen for which the immunoglobulin is specific. Indeed, a functional equivalent of a monoclonal antibody immunoglobulin, for example, may inhibit the binding of the parent monoclonal antibody to its antigen. A functional equivalent may comprise F(ab')2 fragments, F(ab) molecules, Fv fragments, single chain fragment variable displayed on phage (scFv), single domain antibodies, chimeric antibodies, or the like so long as the immunoglobulin exhibits the characteristics of the parent immunoglobulin.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Gene expression" refers to the process by which a polynucleotide sequence undergoes successful transcription and translation such that detectable levels of the nucleotide sequence are expressed.

The term "homology," as used herein, refers to a degree of complementarity. There may be partial homology or complete homology (i.e., identity). A partially complementary sequence is one that at least partially inhibits an identical sequence from hybridizing to a target polynucleotide; it is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

"Individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, woodchucks, ducks, and mice.

"Isolated" refers to a polynucleotide, a polypeptide, an immunoglobulin, or a host cell that is in an environment different from that in which the polynucleotide, the polypeptide, the immunoglobulin, or the host cell naturally occurs.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like. The invention also contemplates the use of radioactive isotopes, such as $^{35}S$, $^{32}P$, $^{3}H$, and the like as labels. Colorimetric labels such as colloidal gold or colored glass or plastic (e.g., polystyrene, polypropylene, latex) beads may also be utilized. See, e.g., U.S. Pat. Nos. 4,366,241; 4,277,437; 4,275,149; 3,996,345; 3,939,350; 3,850,752; and 3,817,837.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

"Polynucleotide" and "nucleic acid," used interchangeably herein, refer to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids. Polynucleotides may further comprise genomic DNA, cDNA, or DNA-RNA hybrids.

"Polypeptide" and "protein," used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

"Predisposition" to a disease or disorder refers to an individual's susceptibility to such disease or disorder. Individuals who are susceptible are statistically more likely to have cancer or fibrosis, for example, as compared to normal/wild type individuals.

The terms "prognosis" and "prognose" refer to the act or art of foretelling the course of a disease. Additionally, the terms refer to the prospect of survival and recovery from a disease as anticipated from the usual course of that disease or indicated by special features of the individual case. Further, the terms refer to the art or act of identifying a disease from its signs and symptoms.

The terms "prognostic indicator" or "indicator" refer to anything that may serve as, or relate to, a ground or basis for a prognosis. These terms further refer to any grounds or basis of a differential diagnosis, including the results of testing and characterization of gene expression as described herein, and the distinguishing of a disease or condition from others presenting similar symptoms. Additionally, the terms "indicator" or "prognostic indicator" refer to any grounds or basis, including the results of testing and characterization of gene expression as described herein, which may be used to distinguish the probable course of a malignant disease.

"Protein-capture agent" refers to a molecule or a multi-molecular complex that can bind a protein to itself. In one embodiment, protein-capture agents bind their binding partners in a substantially specific manner. In one embodiment, protein-capture agents may exhibit a dissociation constant (KD) of less than about $10^{-6}$. The protein-capture agent may comprise a biomolecule such as a protein or a polynucleotide. The biomolecule may further comprise a naturally occurring, recombinant, or synthetic biomolecule. Examples of protein-capture agents include immunoglobulins, antigens, receptors, or other proteins, or portions or fragments thereof. Furthermore, protein-capture agents are understood not to be limited to agents that only interact with their binding partners through noncovalent interactions. Rather, protein-capture agents may also become covalently attached to the proteins with which they bind. For example, the protein-capture agent may be photocrosslinked to its binding partner following binding.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical" The inhibition of hybridization of the completely complementary sequence to the target sequence may be examined using a hybridization assay (Southern or Northern blot, solution hybridization and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

Another way of viewing sequence identity in the context to two nucleic acid or polypeptide sequences includes reference to residues in the two sequences that are the same when aligned for maximum correspondence over a specified region. As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Stringent conditions" refers to conditions under which a probe may hybridize to its target polynucleotide sequence, but to no other sequences. Stringent conditions are sequence-dependent (e.g., longer sequences hybridize specifically at higher temperatures). Generally, stringent conditions are selected to be about 5° C. lower than the thermal melting point ($T_m$) for the specific sequence at a defined ionic strength and pH. The $T_m$ is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e.g., 10 to 50 nucleotides). Stringent conditions may also be achieved with the addition of destabilizing agents, such as formamide.

"Substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% or more free from other components with which it is naturally associated.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e.g., gene or mRNA) whose expression level it is desired to detect.

The terms "treatment," "treating," "treat," and the like refer to obtaining a desired pharmacological and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

b. HF-ASSOCIATED POLYPEPTIDES

In one aspect, the invention relates to "HF-ASSOCIATED polypeptides," which includes polypeptides whose differential expression is associated with hepatic fibrosis. HF-ASSOCIATED polypeptides also include variants of the naturally occurring proteins, where such variants are identical or substantially similar to the naturally occurring protein. In general, variant polypeptides have a sequence that has at least about 80%, usually at least about 90%, and more usually at least about 98% sequence identity with a HF-ASSOCIATED polypeptide described herein, as measured by BLAST. Variant polypeptides can be naturally or non-naturally glycosylated.

In general, variants of the HF-ASSOCIATED polypeptides described herein have a sequence identity greater than at least about 65%, at least about 70%, at least about 75%, at least about 80%, at least about 83%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.9% or may be greater than at least about 99.99% as determined by methods well known in the art, such as BLAST.

In one embodiment, a variant HF-ASSOCIATED polypeptide may be a mutant polypeptide. The mutations in the HF-ASSOCIATED polypeptide may result from, but are not limited to, amino acid substitutions, additions or deletions. The amino acid substitutions may be conservative amino acid substitutions or substitutions to eliminate non-essential amino acids. In general, conservative amino acid substitutions are those that preserve the general charge, hydrophobicity, hydrophilicity, and/or steric bulk of the amino acid substituted.

In some mutant HF-ASSOCIATED polypeptides, amino acids may be substituted to alter a phosphorylation site or an acetylation site.

Importantly, variant polypeptides may be designed so as to retain or have enhanced biological activity of a particular region of the protein (e.g., a functional domain and/or, where the polypeptide is a member of a protein family, a region associated with a consensus sequence). Selection of amino acid alterations for production of variants may be based upon the accessibility (interior vs. exterior) of the amino acid, the thermostability of the variant polypeptide, desired glycosylation sites, desired disulfide bridges, desired metal binding sites, and desired substitutions within proline loops. Cysteine-depleted muteins can be produced as disclosed in U.S. Pat. No. 4,959,314.

Variants also include fragments of the HF-ASSOCIATED polypeptides disclosed herein, particularly biologically active fragments and fragments corresponding to functional domains. Fragments of interest will typically be at least about 10 aa to at least about 15 aa in length, usually at least about 50 aa in length, and can be as long as 300 aa in length or longer. The protein variants described herein are encoded by polynucleotides that are within the scope of the invention.

HF-ASSOCIATED polypeptides of the invention are provided in a non-naturally occurring environment, e.g., are separated from their naturally occurring environment. In certain embodiments, HF-ASSOCIATED protein is present in a substantially purified form.

c. HF-ASSOCIATED AGENTS

Modulators and Binding Partners

In another aspect, the invention provides a "HF-ASSOCIATED agent," which refers to a class of molecules that consists of "HF-ASSOCIATED polypeptide binding partners."

HF-ASSOCIATED polypeptide binding partners are molecules that bind to HF-ASSOCIATED polypeptides. Exemplary polypeptide binding partners are immunoglobulins. Binding partners may, but need not, modulate a HF-ASSOCIATED polypeptide's biological activity.

d. IMMUNOGLOBULINS

HF-ASSOCIATED agents used to identify HF-ASSOCIATED proteins include immunoglobulins and functional equivalents of immunoglobulins that specifically bind to HF-ASSOCIATED polypeptides. The terms "immunoglobulin" and "antibody" are used interchangeably and in their broadest sense herein. Thus, they encompass intact monoclonal antibodies, polyclonal antibodies, multispecific antibodies (e.g., bispecific antibodies) formed from at least two intact antibodies, and antibody fragments, so long as they exhibit the desired biological activity. In one embodiment, the subject immunoglobulins comprise at least one human constant domain. In another embodiment, the HF-ASSOCIATED agent immunoglobulins comprise a constant domain that exhibits at least about 90-95% sequence identity with a human constant domain and yet retains human effector function. An immunoglobulin HF-ASSOCIATED agent or functional equivalent thereof may be human, chimeric, humanized, murine, CDR-grafted, phage-displayed, bacteria-displayed, yeast-displayed, transgenic-mouse produced, mutagenized, and randomized.

i. Antibodies Generally

The terms "antibody" and "immunoglobulin" cover fully assembled antibodies and antibody fragments that can bind antigen (e.g., Fab', F'(ab)$_2$, Fv, single chain antibodies, diabodies), including recombinant antibodies and antibody fragments. Preferably, the immunoglobulins or antibodies are chimeric, human, or humanized.

The variable domains of the heavy and light chain recognize or bind to a particular epitope of a cognate antigen. The term "epitope" is used to refer to the specific binding sites or antigenic determinant on an antigen that the variable end of the immunoglobulin binds. Epitopes can be linear, i.e., be composed of a sequence of amino acid residues found in the primary HF-ASSOCIATED sequence. Epitopes also can be conformational, such that an immunoglobulin recognizes a 3-D structure found on a folded HF-ASSOCIATED molecule. Epitopes can also be a combination of linear and conformational elements. Further, carbohydrate portions of a molecule, as expressed by the target bearing tumor cells can also be epitopes.

Immunoglobulins are said to be "specifically binding" if: 1) they exhibit a threshold level of binding activity, and/or 2) they do not significantly cross-react with known related polypeptide molecules. The binding affinity of an immunoglobulin can be readily determined by one of ordinary skill in the art, for example, by Scatchard analysis (Scatchard, *Ann. NY Acad. Sci.* 51: 660-672, 1949). In some embodiments, the immunoglobulins of the present invention bind to HF-ASSOCIATED at least $10^3$, more preferably at least $10^4$, more preferably at least $10^5$, and even more preferably at least $10^6$ fold higher than to other proteins ii. Polyclonal and Monoclonal Antibodies

Immunoglobulins of the invention may be polyclonal or monoclonal, and may be produced by any of the well known methods in this art.

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized, In addition, aggregating agents such as alum and others are suitably used to enhance the immune response.

The term "monoclonal antibody" refers to an antibody obtained from a population of substantially homogeneous antibodies. Monoclonal antibodies are highly specific, being directed against a single antigenic site. Furthermore, in contrast to polyclonal antibody preparations that typically include different antibodies directed against different determinants, each monoclonal antibody is directed against a single determinant on the antigen.

In addition to their specificity, monoclonal antibodies are advantageous in that they may be synthesized while uncontaminated by other immunoglobulins. For example, monoclonal antibodies may be produced by the hybridoma method or by recombinant DNA methods. Monoclonal antibody HF-ASSOCIATED agents also may be isolated from phage antibody libraries.

iii. Chimeric and Humanized Antibodies

HF-ASSOCIATED polypeptide-binding immunoglobulins or antibodies can be "chimeric" in the sense that a variable region can come from a one species, such as a rodent, and the constant region can be from a second species, such as a human.

"Humanized" forms of non-human HF-ASSOCIATED protein-binding antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody.

In general, the humanized antibody may comprise substantially all of at least one, and typically two, variable domains, in which all or substantially all of the hypervariable loops correspond to those of a non-human immunoglobulin and all or substantially all of the FRs are those of a human immunoglobulin sequence. In one embodiment, humanized antibodies comprise a humanized FR that exhibits at least 65% sequence identity with an acceptor (non-human) FR, e.g., murine FR. The humanized antibody also may comprise at least a portion of an immunoglobulin constant region (Fc), particularly a human immunoglobulin.

Methods for humanizing non-human antibodies have been described in the art. Preferably, a humanized antibody has one or more amino acid residues introduced into it from a source, which is non-human. These non-human amino acid residues are often referred to as "import" residues, which are typically taken from an "import" variable domain. Humanization may be essentially performed by substituting hypervariable region sequences for the corresponding sequences of a human antibody. Accordingly, such humanized antibodies are chimeric wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies. The choice of human variable domains, both light and heavy, to be used in making the humanized antibodies is very important to reduce antigenicity.

Other methods generally involve conferring donor CDR binding affinity onto an antibody acceptor variable region framework. One method involves simultaneously grafting and optimizing the binding affinity of a variable region binding fragment. Another method relates to optimizing the binding affinity of an antibody variable region.

iv. Antibody Fragments

"Antibody fragments" comprise a portion of an intact antibody, preferably the antigen-binding or variable region thereof. Examples of antibody fragments include Fab, Fab', F(ab')$_2$, Fv fragments, diabodies, linear antibodies, single-chain antibody molecules, and multispecific antibodies formed from antibody fragments.

Papain digestion of antibodies produces two identical antigen-binding fragments, called "Fab" fragments, each with a single antigen-binding site, and a residual "Fc" fragment. The Fab fragments also contain the constant domain of the light chain and the first constant domain (CHI) of the heavy chain.

Pepsin treatment yields an F(ab')$^2$ fragment that has two antigen-binding sites and is still capable of crosslinking antigen. Fab' fragments differ from Fab fragments by the addition of a few residues at the carboxy terminus of the heavy chain CHI domain including one or more cysteines from the antibody hinge region. Fab'-SH is the designation herein for Fab' in which the cysteine residue(s) of the constant domains bear at least one free thiol group. F(ab')$^2$ antibody fragments originally were produced as pairs of Fab' fragments which have hinge cysteines between them. Other chemical couplings of antibody fragments are well known in the art.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. The Fv polypeptide may further comprise a polypeptide linker between the VH and VL domains that enables the scFv to form the desired structure for antigen binding. See PLUCKTHUN, 113 THE PHARMACOLOGY OF MONOCLONAL ANTIBODIES 269-315 (Rosenburg and Moore eds. 1994). See also WO 93/16185; U.S. Pat. Nos. 5,587,458 and 5,571,894.

Various techniques have been developed for the production of antibody fragments. Traditionally, these fragments were derived via proteolytic digestion of intact antibodies. However, these fragments may now be produced directly by recombinant host cells.

v. Conjugation and Labeling

Anti-HF-ASSOCIATED protein antibodies may be administered in their "naked" or unconjugated form, or may have other agents conjugated to them.

For examples the antibodies may be in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescent labels (such as FITC or rhodamine, etc.), paramagnetic atoms, and the like. Procedures for accomplishing such labeling are well known in the art.

vi. Bispecific Antibodies

Bispecific antibodies of the invention are small antibody fragments with two antigen-binding sites. Each fragment comprises a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen binding sites.

Methods for making bispecific antibodies are well known in the art. Traditional production of full length bispecific antibodies is based on the coexpression of two immunoglobulin heavy chain-light chain pairs, where the two chains have different specificities.

In another approach, antibody variable domains with the desired binding specificities (antibody-antigen combining sites) may be fused to immunoglobulin constant domain sequences. Specifically, the variable domains are fused with an immunoglobulin heavy chain constant domain, comprising at least part of the hinge, CH2, and CH3 regions. In one embodiment, the fusion protein comprises the first heavy-chain constant region (CHI) because it contains the site necessary for light chain binding. Polynucleotides encoding the immunoglobulin heavy chain fusions and, if desired, the immunoglobulin light chain, may be inserted into separate expression vectors and co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies also have been produced using leucine zippers and single-chain Fv (sFv) dimers.

e. DIAGNOSIS, PROGNOSIS, AND ASSESSMENT OF FIBROSIS THERAPY

In another aspect, therefore, the invention provides methods for using the HF-ASSOCIATED polypeptides described herein to diagnose and prognose fibrosis. In specific non-limiting embodiments, the methods are useful for detecting HF-ASSOCIATED polypeptides in cells or serum/plasma, facilitating diagnosis of fibrosis and the severity of a fibrosis in a subject, facilitating a determination of the prognosis of a subject, determining the susceptibility to fibrosis in a subject, and assessing the responsiveness of the subject to therapy (e.g., by providing a measure of therapeutic effect through, for example, assessing tumor burden during or following a chemotherapeutic regimen). Such methods may involve detection of levels of HF-ASSOCIATED polypeptides in a patient biological sample, e.g., serum/plasma or a suspected or prospective fibrotic tissue or cell. The detection methods of the invention may be conducted in vitro or in vivo, on isolated cells, or in whole tissues or a bodily fluid, e.g., blood, plasma, serum, urine, and the like. In one embodiment, the HF-ASSOCIATED polypeptides may be used to detect and assess fibrosis. These biomarkers may be applied to any disease which displays fibrosis such as hepatic fibrosis, renal fibrosis, cardial fibrosis, skin fibrosis, pancreatic fibrosis etc. but more preferably, the fibrosis is hepatic fibrosis.

f. DETECTING a HF-ASSOCIATED POLYPEPTIDE

Methods are provided for detecting a HF-ASSOCIATED polypeptide in serum. Any of a variety of known methods may be used for detection, including, but not limited to, immunoassay, using antibody specific for the encoded polypeptide, e.g., by enzyme-linked immunosorbent assay (ELISA), radioimmunoassay (RIA), and the like; and functional assays for the encoded polypeptide, e.g., biological activity.

As will be readily apparent to the ordinarily skilled artisan upon reading the present specification, the detection methods and other methods described herein may be readily varied. Such variations are within the intended scope of the invention. For example, in the above detection scheme, the probe for use in detection may be immobilized on a solid support, and the test sample contacted with the immobilized probe. Binding of the test sample to the probe may then be detected in a variety of ways, e.g., by detecting a detectable label bound to the test sample to facilitate detected of test sample-immobilized probe complexes.

The invention further provides methods for detecting the presence of and/or measuring a level of HF-ASSOCIATED polypeptide in a biological sample, using an antibody specific for HF-ASSOCIATED polypeptides. Specifically, the method for detecting the presence of HF-ASSOCIATED polypeptides in a biological sample may comprise the step of contacting the sample with a monoclonal antibody and detecting the binding of the antibody with the HF-ASSOCIATED polypeptide in the sample. More specifically, the antibody may be labeled so as to produce a detectable signal using compounds including, but not limited to, a radiolabel, an enzyme, a chromophore and a fluorophore.

Detection of specific binding of an antibody specific for HF-ASSOCIATED polypeptide, or a functional equivalent thereof, when compared to a suitable control, is an indication that HF-ASSOCIATED polypeptides are present in the sample. Suitable controls include a sample known not to contain HF-ASSOCIATED polypeptides and a sample contacted with an antibody not specific for the encoded polypeptide, e.g., an anti-idiotype antibody. A variety of methods to detect specific antibody-antigen interactions are known in the art and may be used in the method, including, but not limited to, standard immunohistological methods, immunoprecipitation, an enzyme immunoassay, and a radioimmunoassay. In general, the specific antibody will be detectably labeled, either directly or indirectly. Direct labels include radioisotopes; enzymes whose products are detectable (e.g., luciferase, 3-galactosidase, and the like); fluorescent labels (e.g., fluorescein isothiocyanate, rhodamine, phycoerythrin, and the like); fluorescence emitting metals (e.g., 112Eu, or others of the lanthanide series, attached to the antibody through metal chelating groups such as EDTA); chemiluminescent compounds (e.g., luminol, isoluminol, acridinium salts, and the like); bioluminescent compounds (e.g., luciferin, aequorin (green fluorescent protein), and the like). The antibody may be attached (coupled) to an insoluble support, such as a polystyrene plate or a bead. Indirect labels include second antibodies specific for antibodies specific for the encoded polypeptide ("first specific antibody"), wherein the second antibody is labeled as described above; and members of specific binding pairs, e.g., biotin-avidin, and the like. The biological sample may be brought into contact with and immobilized on a solid support or carrier, such as nitrocellulose, that is capable of immobilizing cells, cell particles, or soluble proteins. The support may then be washed with suitable buffers, followed by contacting with a detectably-labeled first specific antibody. Detection methods are known in the art and will be chosen as appropriate to the signal emitted by the detectable label. Detection is generally accomplished in comparison to suitable controls and to appropriate standards.

g. KITS

The detection methods may be provided as part of a kit. Thus, the invention further provides kits for detecting the presence and/or a level of a HF-ASSOCIATED polypeptide in a biological sample. Procedures using these kits may be performed by clinical laboratories, experimental laboratories, medical practitioners, or private individuals. The kits of the invention for detecting a HF-ASSOCIATED polypeptide that is differentially expressed during fibrosis. The kit may provide additional components that are useful in procedures, including, but not limited to, buffers, developing reagents, labels, reacting surfaces, means for detection, control samples, standards, instructions, and interpretive information.

EXAMPLES

Differentially Expressed Proteins Established when Comparing Serum from Normal Healthy Individuals with Fibrosis/Cirrhosis Patients The inventors have discovered that various proteins are differentially expressed in human serum samples of HCV-induced fibrosis/cirrhosis patients when compared with healthy individuals—Gangadharan et al., (2007), Clin. Chem., 53. This discovery was achieved by comparing these serum samples using two dimensional polyacrylamide gel electrophoresis (2D-PAGE), a technique that separates proteins in two dimensions on a gel matrix to give discrete protein spots. This is the first use of a 2D-PAGE approach to identify serum biomarkers for fibrosis.

Example 1

Two Dimensional Polyacrylamide Gel Electrophoresis (2D-PAGE)

To identify biomarkers for different stages of HCV-induced fibrosis, serum samples of healthy individuals and HCV-induced fibrosis/cirrhosis patients (15 individuals) were analysed in a 2D-PAGE-based proteomics study. 500 µg of serum proteins were separated by charge using a pH 3-10 non-linear gradient in the first dimension of the gel and by molecular weight (size) in the second dimension. Electrophoresis, fluorescent staining and scanning of gels were performed as described by Gangadharan et al., (2007), Clin. Chem., 53.

Example 2

Differential Image Analysis and Protein Identification

The two dimensional array of spots generated were compared between normal and fibrosis/cirrhosis serum samples by computer-aided image analysis. Scanned images of all 2D-PAGE gels were analysed by computer-aided image analysis as described by Gangadharan et al., (2007), Clin. Chem., 53. Differentially expressed changes that were greater than or equal to 2-fold different were considered to be significant. A total of 53 differentially expressed features were excised, digested with trypsin, and analysed by mass spectrometry.

Example 3

Figures 1, 2:
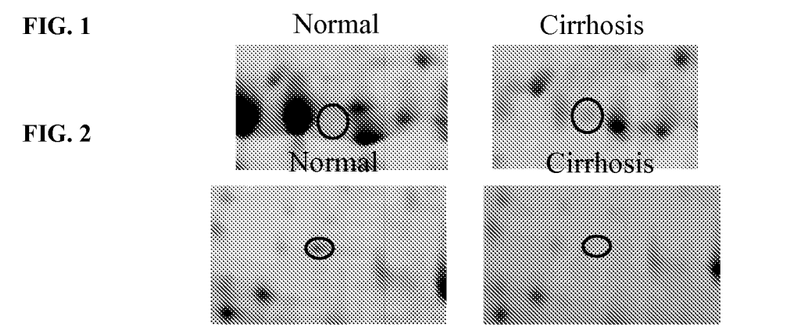
Figure 3:
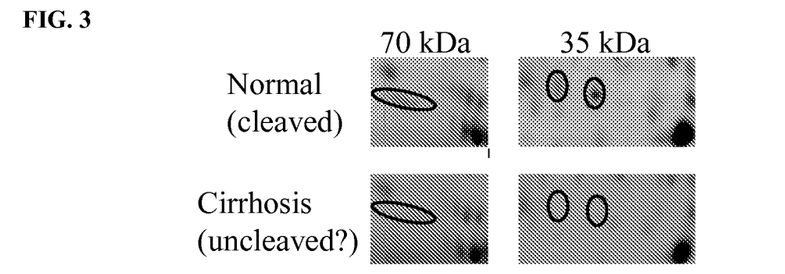
Figure 4:
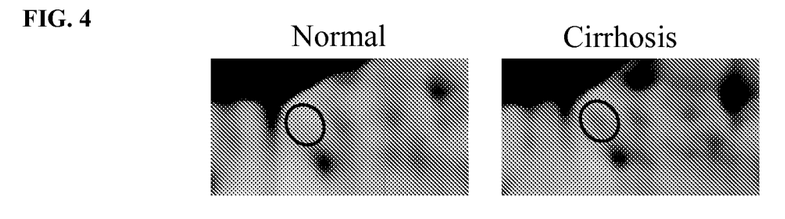
FIG. 4 β2 glycoprotein I is shown to be absent in normal serum but present in serum from cirrhotic patients.
Figure 5:
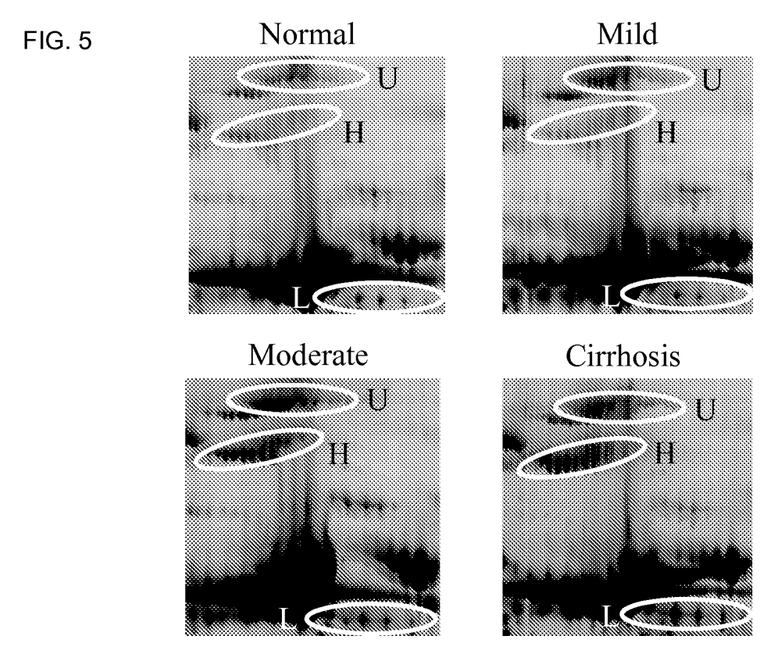
FIG. 5 This figure demonstrates that cleavage of α2 macroglobulin increases with fibrosis. Images shown are magnified images (as in FIGS. 1-4) but shows serum spot profiles from healthy individuals, patients with mild fibrosis, moderate fibrosis and cirrhosis. U shows uncleaved α2 macroglobulin, H shows the heavy chain from cleaved α2 macroglobulin and L shows the light chain from cleaved α2 macroglobulin.

Identification of Human Serum Biomarkers for Hepatic Fibrosis Due to Cirrhosis Differential image analysis revealed initial evidence for potential serum biomarkers. See FIGS. 1-5. The most prominent changes were observed when comparing serum samples from cirrhotic patients with healthy controls. This analysis showed that expression of inter-α-trypsin inhibitor heavy chain H4 fragments (ITIH4), α1 antichymotrypsin, apolipoprotein L1 (Apo L1), prealbumin and albumin was decreased in cirrhotic serum, whereas expression of CD5 antigen like protein (CD5L) and β2 glycoprotein I (β2GPI) increased. In general, α2 macroglobulin (a2M) and immunoglobulin components increased with hepatic fibrosis whereas α1, α2 and β chains of haptoglobin and complement components (C3, C4 and factor H-related protein 1) decreased.

| Patients with Cirhosis | |
|---|---|
| Decrease | Increase |
| inter-α-trypsin inhibitor heavy chain H4 fragments | CD5 antigen like protein (CD5L) |
| α1 antichymotrypsin apolipoprotein L1 (Apo L1) prealbumin and albumin | β2 glycoprotein I (β2GPI) |
| α1, α2 and β chains of haptoglobin and complement components (C3, C4 and factor H-related protein 1) | α2 macroglobulin (a2M) immunoglobulin components |

Example 4

Identification of Human Serum Biomarkers for Hepatic Fibrosis Due to HCV-Induced Fibrosis Novel proteins associated with HCV-induced fibrosis were identified from the differential image analysis. Table 1 provides a summary of selected differentially expressed proteins that have been classified according to their function. These proteins include the inter-α-trypsin inhibitor heavy chain H4 fragments, complement factor H-related protein 1, CD5L, Apo L1, and β2GPI. Increased and decreased thiolester cleavage of a2M and Complement C3, respectively, was also detected. Although β2GPI is a novel biomarker for liver cirrhosis, it has already been observed in Hepatitis B virus (HBV)-mediated liver cancer (Drake et al., (2006), *Mol Cell Proteomics*). The decrease in Complement C3 has also been observed in HBV-mediated liver cancer (Steel et al, (2003), *Proteomics*, 3, 601). These novel proteins may also serve as biomarkers for hepatitis and HCC as well as drug targets for liver fibrosis, e.g. the novel biomarker, inter-α-trypsin inhibitor heavy chain H4, is cleaved by kallikrein a downstream activator of tissue-type plasminogen activator (tPA). tPA is known to be stimulated by drugs presently used in anti-fibrotic therapy (Nagaoka et al., (2003), *Liver Int*, 23, 476; Rimola, (2003), *Am J Transplan*, 5, 433).

| Patients with HCV-induced fibrosis | |
|---|---|
| Decrease | Increase |
| inter-α-trypsin inhibitor heavy chain H4 fragments | CD5L |
| complement factor H-related protein 1 Apo L1 | β2GPI. |
| thiolester cleavage of Complement C3. | thiolester cleavage of a2M |

Example 5

The measurement of these novel proteins in serum will aid reliable diagnosis of both fibrosis and cirrhosis, which may eliminate the need for liver biopsy. These measurements can be achieved using an immunoassay with antibodies targeted against these proteins.

In the case of proteins that have altered cleavage, i.e. a2M, and inter-α-trypsin inhibitor heavy chain H4, the extent of cleavage can be established using N- and C-terminal binding antibodies. An antibody against the cleavage region can determine levels of an uncleaved biomarker. For a2M, two different antibodies can be used: 1) antibodies targeted to the N-terminal end of a2M before the thiolester cleavage site for the larger fragment; and 2) antibodies targeted to the C-terminal end of a2M after the cleavage site for the smaller fragment. Two different antibodies can be used in the case of inter-α-trypsin inhibitor heavy chain H4: 1) antibodies targetting the large 70 kDa chain; and 2) antibodies targetting the small 35 kDa chain. At present there appears to be no commerically available antibodies against the region of the thiolester site of a2M or the active peptide of inter-α-trypsin inhibitor heavy chain H4 where cleavage occurs. The antibody against the cleavage region can more reliably help to determine levels of the intact and cleaved biomarkers.

Example 6

A fibrosis scoring scale for each of the novel biomarkers can be formulated. The average concentration of these biomarkers in serum over the various stages of liver fibrosis is determined. A scale of 0 to 6 is presently used to assess liver fibrosis in the clinic where 0 represents no fibrosis, 1-5 represent the intermediate stages of fibrosis in increasing severity from mild to moderate/severe and 6 is cirrhosis (Ishak, (1995), *J Hepatol*, 22, 696). By determining the concentration ranges of the novel biomarkers across these seven stages, a similar scoring system of 0 to 6 can be assigned. The additive results from the scores of all the novel biomarkers give a more reliable indication of the degree of fibrosis rather than examining individual biomarkers.

Example 7

ELISA Assay

An Enzyme Linked Immunosorbent Assay (ELISA) is used measure the novel fibrosis biomarkers. This is an assay performed in 96-well plate format. One option is to use the non-competitive one-site binding ELISA. In this assay, known concentrations of antigen (in this example, the novel biomarkers and serum samples) are prepared in a bicarbonate buffer, added to the 96-well plate and incubated overnight at 4° C. The wells are then washed three times with a solution of phosphate buffered saline (PBS) and Tween (PBS-T) followed by blocking with a PBS solution containing bovine serum albumin (BSA). After incubating at 37° C. for 1 hour, a primary antibody directed against the antigen (in this example, the biomarker of interest) is added, the plate incubated at 37° C. for 1 hour and then washed three times with PBS-T. A horseradish peroxidase (HRP)-conjugated secondary antibody, directed against the animal origin of the primary antibody, is then added, and the plate incubated at 37° C. for 1 hour followed by three washes with PBS-T. Finally, a peroxidase substrate such as 2,2'-azino-bis(3-ethylbenzthiazoline-6-sulphonic acid) (ABTS) is added to each well and the absorbance read on a plate reader at 405 nm after 30 minutes.

Alternatively, a sandwich ELISA can be used. In this type of assay, one antibody is bound to the bottom of a plate well. The antigen, in this case the biomarker protein, is added and unbound products are removed by washing. A second, labeled antibody that binds to the antigen is then added. The amount of bound secondary antibody is quantified, usually calorimetrically. In addition to the novel biomarkers, the inventors propose that haptoglobin can be measured by ELISA. The levels of haptoglobin in serum, in conjunction with liver function tests (LFTs) determined by clinicians, will establish a more reliable score for liver fibrosis.

TABLE 1

Summary of selected differentially expressed proteins identified in serum samples of healthy controls vs. the different stages of hepatic scarring. [a]

| Classification | Protein Name | Changes in Relation to Controls | | | Protein Function |
| | | Mild | Moderate | Cirhosis | |
| --- | --- | --- | --- | --- | --- |
| Plasmin-assoctaed | a2M | ↑ | → | ↑→ | Inhibits plasmin |
| | ITIH4 | — | — | ↓← | Can be cleaved by kallikrein (leads to plasma activation) |
| Decreased because of compromise in hepatic synthetic function | Albumin | — | — | ↓ | Liver synthesized protein; most abundant protein in serum |
| | Prealbumin (transthyrein) | — | — | ↓ | Liver synthesized protein; carries vitamin A |
| | Complement C3, C4 and factor H-related protein 1 | ← | ↓ | ↓← | Liver synthesized protein; involved in complement cascade |
| HGF-related | α1 antichymotrypsin | — | — | ↓ | HGF decreases α1 antichymotrypsin |
| | Haptoglobin | ↓ | ↓ | ↓← | HGF decreases haptoglobin synthesis |
| Lipid metabolism | Apo L1 | — | — | ← | Concentrations correlate with triglycerides and cholesterol |
| | β2GP1 | — | — | → | Binds to chylomicrons and HDLs |
| | Panoxonase/arylesterase 1 | — | — | ↓ | Degrades oxidized lipids in lipoproteins and cells |
| | Zinc-α2-glycoprotein | — | — | ↓ | Stimulates lipolysis in adipocytes |
| Immune system related | CD5 antigen-like | — | — | → | Possible immune system regulation role; IgM related |
| | IgA1 + IgG2 heavy chain and Ig light chain regions | — | ↑ | ↑→ | Immunoglobin fragments |

[a] Proteins shown were differentially expressed by 2-fold or more when comparing serum gels from healthy controls with the different stages of hepatic fibrosis.
→, present only in serum from hepatic scarring patients.
↑, present in serum from both control and hepatic scarring patients but expressed to a higher extent in hepatic scarring.
—, no significant change.
↓, present in serum from both control and hepatic scarring patients but expressed to a higher extent in control serum
←, present only in serum from healthy controls.

What is claimed is:

1. A method of diagnosing hepatic fibrosis comprising:
   a) obtaining a biological sample from a subject in need thereof;
   b) detecting in said biological sample i) a level of apolipoprotein L1 (ApoL1) and ii) a level of at least one HF-ASSOCIATED polypeptide selected from the group consisting of: inter-α-trypsin inhibitor heavy chain H4 fragments, α1 antichymotrypsin, prealbumin, isoforms of CD5 antigen like protein (CD5L), β2 glycoprotein I (β2GPI), thioester cleaved α2 macroglobulin (a2M) and immunoglobulin components, α1, α2 and β chains of haptoglobin, complement components C3 and factor H-related protein 1, ApoE, clusterin, and angiotensinogen; and
   c) diagnosing hepatic fibrosis in said subject by comparing said level of apolipoprotein L1 and said level of the at least one HF-ASSOCIATED polypeptide detected in said biological sample to a control level of apolipoprotein L1 and a control level of said HP-ASSOCIATED polypeptide, respectively,
   wherein a decrease in the level of, or absence of inter-α-trypsin inhibitor heavy chain H4 fragments, prealbumin, complement components C3 and factor H-related protein 1, α1 antichymotrypsin, α1, α2 and β chains of haptoglobin, and ApoL1, corresponds to hepatic fibrosis,
   wherein an increase in the level of, or presence of thioester cleaved a2M and immunoglobulin components, β2GPI, and isoforms of CD5 antigen like protein, corresponds to hepatic fibrosis.

2. The method of claim 1, wherein the biological sample is serum.

3. A method for scaling the severity of hepatic fibrosis comprising:
   a) obtaining a biological sample from a subject in need thereof;
   b) detecting in said biological sample i) a concentration of apolipoprotein L1 (ApoL1) and ii) a concentration of at least one HF-ASSOCIATED polypeptide selected from the group consisting of: inter-α-trypsin inhibitor heavy chain H4 fragments, α1 antichymotrypsin, prealbumin, isoforms of CD5 antigen like protein (CD5L), β2 glycoprotein (β2GPI), thioester cleaved α2 macroglobulin (a2M) and immunoglobulin components, α1, α2 and β chains of haptoglobin, complement components C3 and factor H-related protein 1, ApoE, clusterin, and angiotensinogen
   c) comparing said concentration of apoliprotein L1 and said concentration of the at least one HF-ASSOCIATED polypeptide detected in said biological sample to a predetermined concentration of apolipoprotein L1 and a predetermined concentration of said at least one HF-ASSOCIATED polypeptide, respectively, in a population of patients ranging from no fibrosis to cirrhosis; and d) scaling the severity of hepatic fibrosis by determining concentration ranges of apolipoprotein L1 and the at least one HF-ASSOCIATED polypeptide across no fibrosis, representing a score of 0, to cirrhosis, representing a score of 6, wherein a decrease in the concentration of, or absence of inter-α-trypsin inhibitor heavy chain H4 fragments, prealbumin, complement components C3 and factor H-related protein 1, α1 antichymotrypsin, α1, α2 and β chains of haptoglobin, and ApoL1, corresponds to hepatic fibrosis;

wherein an increase in the concentration of, or presence of thioester cleaved a2M and immunoglobulin components, β2GPI, and isoforms of CD5 antigen like protein, corresponds to hepatic fibrosis.

4. The method of claim 1, wherein the at least one HF-ASSOCIATED polypeptide is inter-α-trypsin inhibitor heavy chain H4 fragments.

5. The method of claim 1, wherein the at least one HF-ASSOCIATED polypeptide is β2 glycoprotein I (β2GPI).

6. The method of claim 1, wherein the at least one HF-ASSOCIATED polypeptide is thioester cleaved α2 macroglobulin (a2M).

7. The method of claim 1, wherein the at least one HF-ASSOCIATED polypeptide is ApoE.

8. The method of claim 1, wherein the at least one HF-ASSOCIATED polypeptide is prothrombin.

9. The method of claim 1, wherein the at least one HF-ASSOCIATED polypeptide is clusterin.

10. The method of claim 1, wherein the at least one HP-ASSOCIATED polypeptide is angiotensinogen.

11. The method of claim 1, wherein the at least one HF-ASSOCIATED polypeptide is complement components C3.

12. The method of claim 3, wherein the biological sample is a serum sample or a plasma sample from the subject.

13. The method of claim 1, wherein said detecting comprises using a first agent that is specific to apolipoprotein L1 and a second agent that is specific to the at least one HF-associates polypeptide.

14. The method of claim 3, wherein said detecting comprises using a first agent that is specific to apolipoprotein L1 and a second agent that is specific to the at least one HF-associated polypeptide.

15. The method of claim 1, wherein the at least one HF associated biomarker is selected from the group consisting of inter-α-trypsin inhibitor heavy chain H4 fragments, α1 antichymotrypsin, prealbumin, isoforms of CD5 antigen like protein (CD5L), β2 glycoprotein I (β2GPI), thioester cleaved α2 macroglobulin (a2M) and immunoglobulin components, α1, α2 and β chains of haptoglobin, factor H-related protein 1, and angiotensinogen.

16. The method of claim 3, wherein the at least one HF associated biomarker is selected from the group consisting of inter-α-trypsin inhibitor heavy chain H4 fragments, α1 antichymotrypsin, prealbumin, isoforms of CD5 antigen like protein (CD5L), β2 glycoprotein I (β2GPI), thioester cleaved α2 macroglobulin (a2M) and immunoglobulin components, α1, α2 and β chains of haptoglobin, factor H-related protein 1, and angiotensinogen.

17. The method of claim 13, wherein said first agent is an antibody that binds apolipoprotein L1 and said second agent is an antibody that binds the at least one HF-ASSOCIATED polypeptide.

18. The method of claim 13, wherein said detecting is performed by an assay technique.

19. The method of claim 18, wherein said assay technique is enzyme-linked immunosorbent assay or radioimmunoassay.

20. The method of claim 14, wherein said first agent is an antibody that binds apolipoprotein L1 and said second agent is an antibody that binds the at least one HF-ASSOCIATED polypeptide.

21. The method of claim 14, wherein said detecting is performed by an assay technique.

22. The method of claim 21, wherein said assay technique is enzyme-linked immunosorbent assay or radioimmunoassay.

\* \* \* \* \*